United States Patent
Diehm et al.

(10) Patent No.: US 10,015,872 B2
(45) Date of Patent: Jul. 3, 2018

(54) SHIFTING MECHANISM FOR DUAL X-RAY TUBE IMAGING SYSTEM

(71) Applicant: Avonix Imaging, LLC, Maple Grove, MN (US)

(72) Inventors: Jeffrey Diehm, Columbia Heights, MN (US); Brian Ruether, Zimmerman, MN (US); Joel Ostby, Edina, MN (US)

(73) Assignee: Avonix Imaging, LLC, Maple Grove, MN (US)

( * ) Notice: Subject to any disclaimer, the term of this patent is extended or adjusted under 35 U.S.C. 154(b) by 205 days.

(21) Appl. No.: 15/220,851

(22) Filed: Jul. 27, 2016

(65) Prior Publication Data

US 2018/0035523 A1 Feb. 1, 2018

(51) Int. Cl.
*A61B 6/00* (2006.01)
*G01N 23/04* (2018.01)
*H05G 1/02* (2006.01)

(52) U.S. Cl.
CPC ............ *H05G 1/02* (2013.01); *A61B 6/4007* (2013.01); *A61B 6/54* (2013.01); *G01N 23/04* (2013.01); *G01N 2223/308* (2013.01); *G01N 2223/309* (2013.01); *G01N 2223/3302* (2013.01); *G01N 2223/423* (2013.01)

(58) Field of Classification Search
CPC ........ A61B 6/4007; A61B 6/54; G01N 23/04; G01N 2223/308; G01N 2223/309; G01N 2223/3302; G01N 2223/423; H05G 1/02
See application file for complete search history.

(56) References Cited

U.S. PATENT DOCUMENTS

| | | | |
|---|---|---|---|
| 2008/0095308 A1* | 4/2008 | Kano | A61B 6/022 378/41 |
| 2008/0192890 A1* | 8/2008 | Nisius | G01N 23/04 378/57 |
| 2010/0310038 A1* | 12/2010 | Behling | A61B 6/032 378/9 |
| 2012/0082290 A1* | 4/2012 | Flohr | A61B 6/027 378/8 |
| 2014/0039303 A1* | 2/2014 | Kanzaki | A61B 6/12 600/424 |
| 2015/0170361 A1* | 6/2015 | Wang | A61B 6/5205 378/9 |
| 2015/0369759 A1* | 12/2015 | Mazor | G01N 23/201 378/89 |

(Continued)

*Primary Examiner* — Mark R Gaworecki
(74) *Attorney, Agent, or Firm* — Winthrop & Weinstine, P.A.

(57) ABSTRACT

A x-ray tube mounting assembly, including a mounting bracket, a first x-ray tube support configured for supporting a first x-ray tube, a second x-ray tube support configured for supporting a second x-ray tube, and a control assembly for moving the first and second x-ray tube supports substantially simultaneously between a first position, wherein the first x-ray tube support is in an operating position and the second x-ray tube support is in a first stowed position not for operation of a second x-ray tube operably supported thereby, and a second position, wherein the second x-ray tube support is in the operating position and the first x-ray tube support is in a second stowed position not for operation of a first x-ray tube operably supported thereby. The first x-ray tube may be of different focus source magnitude than the second x-ray tube.

20 Claims, 5 Drawing Sheets

(56) References Cited

U.S. PATENT DOCUMENTS

| | | | |
|---|---|---|---|
| 2016/0081641 A1* | 3/2016 | Bouhnik | G06T 7/97 378/5 |
| 2016/0157955 A1* | 6/2016 | Torigoe | A61B 90/39 378/42 |
| 2016/0220207 A1* | 8/2016 | Jouhikainen | A61B 6/482 |
| 2017/0197098 A1* | 7/2017 | Hirasawa | A61N 5/1077 |

* cited by examiner

SHIFTING MECHANISM FOR DUAL X-RAY TUBE IMAGING SYSTEM

FIELD OF THE INVENTION

The present disclosure relates to novel and advantageous systems and methods for imaging systems, and particularly to systems and methods for use with imaging systems having more than one x-ray tube.

BACKGROUND OF THE INVENTION

Oftentimes, one or more objects or components may need to be, or are desired to be, internally inspected in order to obtain information regarding the component that is not visually available on an exterior inspection, to identify the internal structure of the component, to view structural fractures or other failures of the component, or to review the inner workings of the component. Components may include parts of products or entire products. One way to inspect components for these and other similar issues is with digital radiography (DR) x-ray and x-ray computed tomography (CT) scans. For such scans, the component may often be positioned on a platform, in some cases a rotatable platform, between an x-ray tube and an x-ray detector. The x-ray tube transmits an x-ray beam against and through the component that is detected by the x-ray detector and converted into a visual image for inspection. The x-ray beam may have a focal point. For an inspection of the component from multiple angles thereof, the component may be rotated about a rotational axis that usually needs to remain aligned with the focal point of the x-ray beam. The position of the component relative to the x-ray tube is important to obtain a desired image of the component for an area of interest.

In some instances, it may be desirable to obtain images of the component using x-ray beams of different magnitudes or x-ray sources that vary in some other property such as but not limited to, focal spot size, which means using different x-ray tubes. This may require moving the component from one imaging system with one x-ray tube of one magnitude to another imaging system with another x-ray tube of a different magnitude (or another x-ray source that varies in a different property). That is, the component is physically moved from one system to the next, and this can take considerable time to correctly position the component relative to the x-ray tubes.

In some embodiments, multiple x-ray tubes may be used to transmit x-ray beams at different magnitudes within the same imaging system. Typically, one of the x-ray tubes has a higher magnitude, and may be larger in size, than at least one of the other tubes. The x-ray tubes may also have different focal points. Usually only one x-ray tube is used at a time, and typically switching between x-ray tubes requires repositioning of at least one or more of the x-ray tubes. In some embodiments, one x-ray tube may be mounted opposite the x-ray detector, and may be unmounted and replaced with another x-ray tube within the same imaging system. However, this can also be a time consuming and inefficient task. In some embodiments, multiple x-ray tubes may be mounted onto swing arms within the same imaging system, and a user may rotate one of the x-ray tubes out of the imaging area and then move the desired x-ray tube into place. These systems conventionally only permit repositioning of the x-ray tubes independently of one another. Moreover, it may be cumbersome to move the x-ray tubes out of the way of one another because of their relative size. Still further, this arrangement typically requires a larger footprint for the imaging system in order to swing out one of the x-ray tubes. Moving the x-ray tubes in and out of position in this manner may also result in one of the x-ray tubes undesirably making contact with the component to be imaged, forcing the component to be imaged out of position. The component to be imaged may, thus, need to be repositioned in order to realign the component with the focal point of the selected x-ray tube. Even if the potential for contact was not an issue, where the focal points of the x-ray tubes are not similarly aligned, the component to be imaged would nonetheless need be repositioned in order to align the rotational axis of the component with the new focal point.

Therefore, it would be desirable to have an imaging system where the component to be imaged does not need to be repositioned when switching between x-ray tubes of the imaging system. It would be further desirable to have an imaging system with multiple x-ray tubes having a more efficient footprint, and where the x-ray tubes can be moved into and out of position without obstructing or contacting the component to be imaged. It also would be desirable to have an imaging system where moving one x-ray tube out of position generally simultaneously moves the newly desired x-ray tube into position, particularly in a manner such that the focal point of the x-ray tube moving into position aligns to the spot where the focal point of the x-ray tube moving out of position was, such that the component to be imaged need not be repositioned.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one embodiment, relates to a component imaging system including a frame and mounting assembly. The frame can include a first upright, a second upright for mounting a x-ray detector, and a base operably connecting the first and second uprights. The mounting assembly may be provided on the first upright and may include a first x-ray tube support configured for supporting a first x-ray tube, a second x-ray tube support configured for supporting a second x-ray tube, and a control assembly for moving the first and second x-ray tube supports substantially simultaneously between a first position, wherein the first x-ray tube support is in an operating position and the second x-ray tube support is in a first stowed position not for operation of a second x-ray tube operably supported thereby, and a second position, wherein the second x-ray tube support is in the operating position and the first x-ray tube support is in a second stowed position not for operation of a first x-ray tube operably supported thereby. The first x-ray tube support may be configured for supporting a x-ray tube of different focus source magnitude than the second x-ray tube support is configured to support. In some embodiments, the mounting assembly may include a mounting bracket, and means for slidable engagement between the mounting bracket and the first and second x-ray tube supports. The means for slidable engagement may be a track operably connected with the mounting bracket and one or more guides operably connected with the first and second x-ray tubes, the one or more guides slidably engaging the track. In some embodiments, a ramp may be positioned on the mounting bracket at a nonparallel angle to the track. The first x-ray tube support may include a cam follower for engaging with the ramp as the first x-ray tube support is slidingly repositioned in a first direction along the track. Engagement of the cam follower with the ramp as the first x-ray tube support is slidingly repositioned in the first direction along the track may cause the first x-ray tube support to additionally move in a direction nonparallel, and specifically perpendicular in some cases, to the first direction. The component imaging system may be configured such that in the first position, a focal point of a first x-ray tube supported by the first x-ray tube support is in substantially the same position as is a focal point of a second x-ray tube supported by the second x-ray tube support in the second position. The control assembly, in some embodiments, may be a relatively simple hand crank and ball screw.

The present disclosure, in another embodiment, relates to a x-ray tube mounting assembly, including a mounting bracket, a first x-ray tube support configured for supporting a first x-ray tube, a second x-ray tube support configured for supporting a second x-ray tube, and a control assembly for moving the first and second x-ray tube supports substantially simultaneously between a first position along the mounting bracket, wherein the first x-ray tube support is in an operating position and the second x-ray tube support is in a first stowed position not for operation of a second x-ray tube operably supported thereby, and a second position, wherein the second x-ray tube support is in the operating position and the first x-ray tube support is in a second stowed position not for operation of a first x-ray tube operably supported thereby. Again, the first x-ray tube support may be configured for supporting a x-ray tube of different focus source magnitude than the second x-ray tube support is configured to support. The mounting assembly may include means for repositioning the first and second x-ray tube supports in a first direction along the mounting bracket. The mounting bracket may include a ramp positioned at a nonparallel angle to the first direction. The first x-ray tube support may include a cam follower for engaging with the ramp as the first x-ray tube support is repositioned in the first direction along the mounting bracket. Engagement of the cam follower with the ramp as the first x-ray tube support is repositioned in the first direction along the track may cause the first x-ray tube support to be additionally repositioned in a direction nonparallel, and specifically perpendicular in some cases, to the first direction. The mounting assembly may be configured such that in the first position, a focal point of a first x-ray tube supported by the first x-ray tube support is in substantially the same position as is a focal point of a second x-ray tube supported by the second x-ray tube support in the second position.

The present disclosure, in still another embodiment, relates to a method for positioning a first x-ray tube and a second x-ray tube relative to a component to be imaged in a digital radiography or computed tomography imaging system. The method may include adjusting the position of a first x-ray tube support, supporting the first x-ray tube, from a stowed position to an operating position by moving the first x-ray tube support along an angled ramp assembly, wherein a focal point of the first x-ray tube moves from a first position in the stowed position to a second position in the operating position, wherein the second position of the focal point of the first x-ray tube is substantially the same as a position of the focal point of the second x-ray tube when the first x-ray tube is in the stowed position. Adjusting the position of the first x-ray tube support may involve moving the first x-ray tube support generally simultaneously in at least two non-parallel directions. The method may further include generally simultaneously moving the second x-ray tube support in at least one of the non-parallel directions.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying figures, in which:

DETAILED DESCRIPTION

The present disclosure relates to novel and advantageous systems and methods for inspecting components using digital radiography (DR) x-ray or x-ray computed tomography (CT) scan technology. More particularly, the present disclosure relates to a mounting assembly for shifting between at least two x-ray tubes of an inspection or imaging system.

Figure 1:
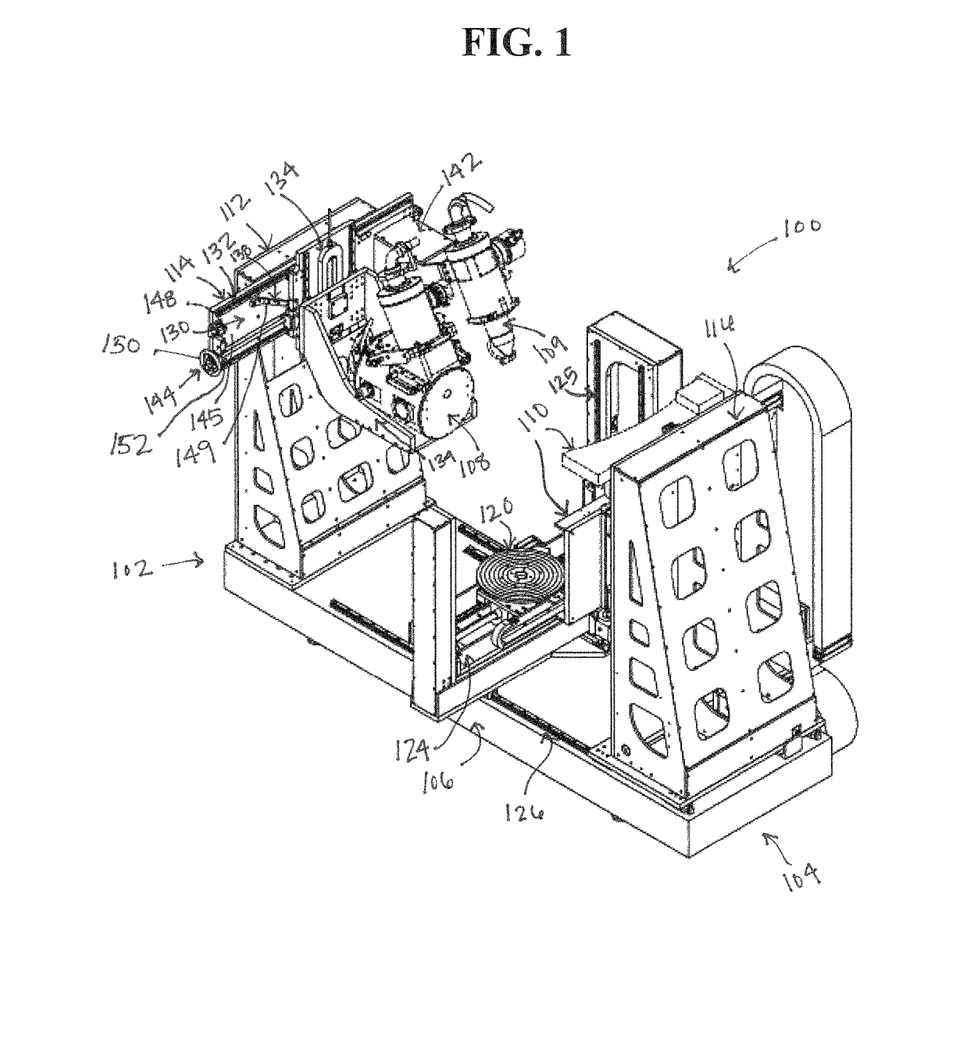
FIG. 1 is an isometric view of one embodiment of a component inspection system of the present disclosure.

FIG. 1 shows one embodiment of a large envelope component imaging system 100 of the present invention having an x-ray tube mounting assembly, which may have at least one x-ray tube movable between a stowed position and a desired operating position. Although embodiments of the x-ray tube mounting assembly are shown herein with respect to large envelope component imaging systems, the x-ray tube mounting assemblies as described herein may also be suited for cabinet-style imaging systems using multiple x-ray tubes.

As shown in FIG. 1, the component imaging system 100 may comprise a first end 102, a second end 104, and a base 106 therebetween. In some embodiments, the base 106 may comprise a solid floor or it may comprise rails that connect the first end 102 to the second end 104 in a longitudinal direction. In at least one embodiment, a primary x-ray tube 108 and a secondary x-ray tube 109 may each be mounted at the first end 102. The primary x-ray tube 108 and the secondary x-ray tube 109, in some embodiments, may have different sizes and/or different focus source magnitudes relative to one another. In other embodiments, the primary x-ray tube 108 and the secondary x-ray tube 109 may vary in some other property such as but not limited to, focal spot size. Thus, while discussed throughout the remainder of this application with regard to varying in physical size and/or focus source magnitude, it is to be understood that the various embodiments of the present disclosure are intended to include instances where the primary x-ray tube 108 and the secondary x-ray tube 109 have different sizes and/or different focus source magnitudes relative to one another and/or may vary in some other property. The terms "primary" and "secondary" (as well as "first" and "second," or the like) are used herein to reference each of the x-ray tubes (or other corresponding elements) but the terms are not intended to be limiting or connotate anything about order of significance between the two x-ray tubes (or other corresponding elements). In at least one embodiment, one of the x-ray tubes (e.g. the primary x-ray tube 108) may be larger in size than the other of the x-ray tubes (e.g. the secondary x-ray tube 109), but in other embodiments the primary x-ray tube 108 may be the same size or be smaller in size than the secondary x-ray tube 109. In some embodiments, the x-ray tubes 108, 109 may each have a focus source magnitude selected from the group comprising 160 kV, 225 kV, 320 kV, 450 kV and 750 kV, but in other embodiments, each of the x-ray tubes may have any suitable focus source magnitude. In at least one embodiment, one of the x-ray tubes (e.g., the primary x-ray tube 108) may have a greater focus source magnitude than the other of the x-ray tubes (e.g., the secondary x-ray tube 109), but in other embodiments, the primary x-ray tube 108 may have the same or smaller focus source magnitude than the secondary x-ray tube 109.

At least one x-ray detector 110 may be mounted at the second end 104 opposite the x-ray tubes 108, 109. The x-ray tubes 108, 109 may be mounted to a first upright 112 via a mounting assembly 114. The at least one x-ray detector 110 may be mounted to a second upright 116. The x-ray tubes 108, 109 may each be any suitable x-ray tube for emitting the desired x-ray beam for analysis and inspection of components. An x-ray detector 110 may be any detector compatible with x-ray tubes 108, 109. In some embodiments, the mounting assembly 114 may engaged with a track assembly that allows movement of the mounting assembly 114 in a vertical direction along the first upright 112 relative to the base 106. In this way, both x-ray tubes 108, 109 may be moved vertically with movement of the mounting assembly 114 along the track assembly.

A platform 120 for holding a component for inspection may be positioned generally between the x-ray tubes 108, 109 and the at least one x-ray detector 110. The platform 120 may be positioned on, or otherwise connected to, the base 106 along a track assembly 124. In one embodiment, the platform 120 may be rotatable about a central rotational axis of the foundation perform 120. The platform 120 may be moved along the track assembly 124 in a direction perpendicular to the longitudinal direction of the base 106, for positioning the platform to any suitable position across a width of the base. In one embodiment, the track assembly 124 may slidably engaged with a track assembly 125 and be moved vertically with respect to the base along a track assembly 125. The track assembly 124 may additionally or alternatively be slidably engaged with a track assembly 126 for moving the platform 120 towards and away from the x-ray tubes 108, 109 and/or the x-ray detector 110. In still further embodiments, the platform 120 may be tiltable or rotatable about a longitudinal axis of the track assembly 124. In at least one embodiment, the second upright 114 may also be slidably engaged with the track assembly 126 for moving the x-ray detector 110 towards and away from the x-ray tube 108, individually or in combination with the platform 120. In still other embodiments, the first upright 112 may also be slidably engaged with a track assembly for movement of the x-ray tube 108 relative the x-ray detector 110 and/or the platform 120. A component for inspection may be positioned on top of the platform 120.

An x-ray tube mounting assembly 114 may comprise a mounting bracket 130, a first track assembly 132, a first x-ray tube support 134, a ramp assembly 138, a second x-ray tube support 142, and a control assembly 144. The mounting bracket 130 may be attached to the upright 112 by any suitable securing mechanism now known or later discovered, including but not limited to, welds, bolts, screws, brackets, etc. The first track assembly 132 and the ramp assembly 138 may be mounted to the mounting bracket 130 onto or into, or formed integrally with, a first side 145 of the mounting bracket. In one embodiment, the first track assembly 132 may comprise at least two rails 148 mounted or otherwise disposed in parallel to one another. The first x-ray tube support 134 and the second x-ray tube support 142 may engage with the rails 148 of the first track assembly 132. Engagement with the rails 148 of the first track assembly 132 allows for movement of each of the first x-ray tube support 134 and the second x-ray tube support 142 in a generally horizontal direction along the first track assembly 132. Engagement with the first track assembly 132 also allows the first x-ray tube support 134 and the second x-ray tube support 142 to each be supported, and in some cases removably supported, by the mounting bracket 130. The x-ray tube supports 134, 142 may each be designed to hold at least one x-ray tube 108, 109 in a substantially fixed position. In other embodiments, x-ray tubes may be pivotably, tiltably, rotatably, or otherwise movably mounted to the x-ray tube supports 134, 142. In at least one embodiment, at least the first x-ray support 134 may be engaged via a cam follower with the ramp assembly 138, as will be described in detail below. The ramp assembly 138 may comprise at least one ramp 149, as will also be described in detail below. Because of the relative position of the ramp assembly 138 on the mounting bracket 130, when the first x-ray tube support 134 is engaged with the ramp assembly, as the first x-ray tube support is moved along first track assembly 132, the first x-ray tube support 134 may substantially simultaneously move in both a horizontal and vertical direction relative to its initial position along the first track assembly 132 and the ramp assembly 138.

The control assembly 144 controls movement of the x-ray tube supports 134, 142 along the first track assembly 132. The control assembly 144, as shown, may comprise a hand crank 150 and a ball screw 152 operably connected with the hand crank 150 and rotatable therewith. The ball screw 152 may be operably attached to the first x-ray tube support 134. Rotation of the hand crank 150 in a first direction moves at least the first x-ray tube support 134 in a first direction toward the desired operating position, and rotation of the hand crank 150 in a second direction moves at least the first x-ray tube support 134 in a second direction opposite the first direction to return the first x-ray tube support 134 to the stowed position. In some embodiments, the control assembly 144 may comprise a motor for electrical control of the movement of the x-ray tube support 134. In at least one embodiment, the motor provides rotational motion to rotate the ball screw of the control assembly. Other control assemblies that can drive linear motion of one or more of the x-ray tube supports 134, 142 are contemplated, and include but are not limited to hydraulic drive systems, pneumatic drive systems, rack and pinion systems or other gear systems, etc.

Figure 2A:
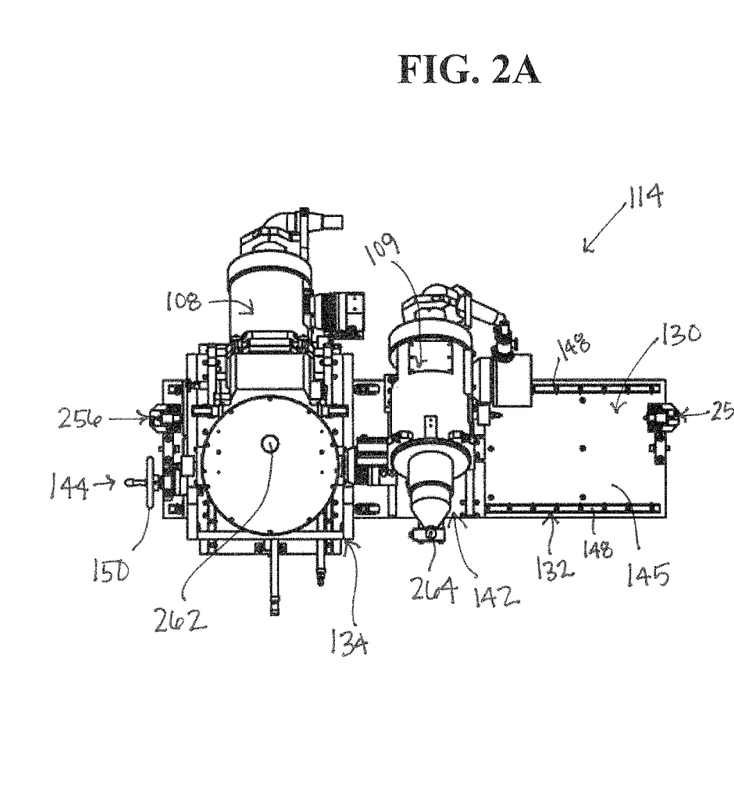
FIG. 2A shows a front view of one embodiment of a mounting assembly of the present disclosure with a primary x-ray tube in a stowed position.
Figure 2B:
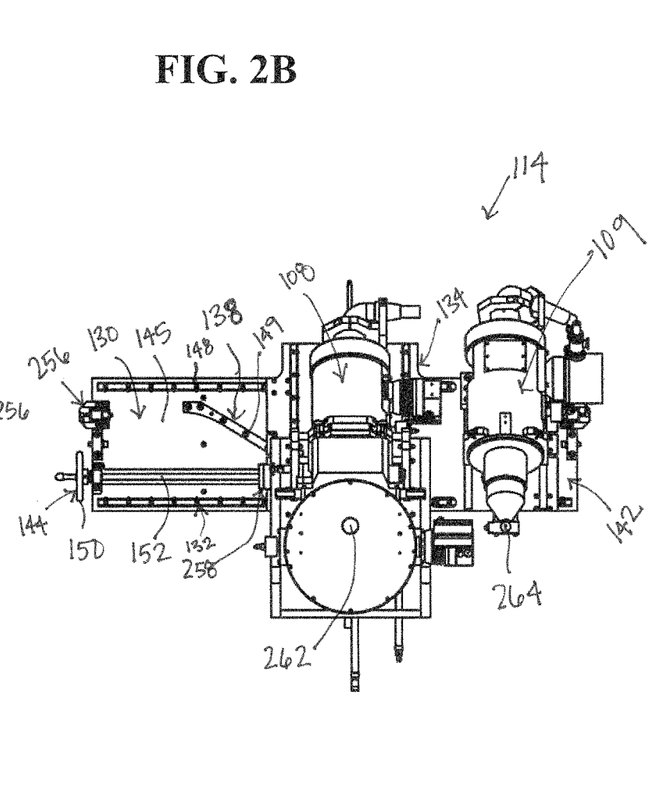
FIG. 2B shows a front view of the mounting assembly shown in FIG. 2A with the primary x-ray tube in a desired operating position.

FIGS. 2A and 2B show more detail of an x-ray tube mounting assembly 114, with a primary x-ray tube in a stowed position and a desired operating position, respectively. As shown in FIGS. 2A and 2B, the x-ray tube mounting assembly 114 comprises primary x-ray tube 108, secondary x-ray tube 109, mounting bracket 130, a first track assembly 132, a first x-ray tube support 134 for holding the primary x-ray tube 108, a ramp assembly 138, a second x-ray tube support 142 for holding the secondary x-ray tube 109, a control assembly 144, and one or more stops 256. A stop 256 may be positioned at one or both ends of the mounting bracket 130 to limit horizontal movement of the first x-ray tube support 134 and/or the second x-ray tube support 142 along the first track assembly 132. In at least one embodiment, the stops 256 may be positioned to prevent movement of the first x-ray tube support 134 or the second x-ray tube support 142 beyond the ends of the mounting bracket 130. In at least the embodiment shown, the ramp assembly 138 is positioned on the mounting bracket 130 between rails 148 of the first track assembly 132. The control assembly 144, as shown, may comprise a hand crank 150 and a ball screw 152 operably connected with the hand crank 150 and rotatable therewith. The ball screw 152 may connect to a linking member 258 of at least one of the first x-ray tube support 134 and the second x-ray tube support 142. In at least one embodiment, the control assembly 144 may be positioned on the mounting bracket 130 between rails 148 of the first track assembly 132. In at least one embodiment, the control assembly 144 may be positioned on the mounting bracket 130 below the ramp assembly 138. The primary x-ray tube 108 has a focal point 262, and the secondary x-ray tube has a focal point 264.

With the primary x-ray tube 108 in the stowed position shown in FIG. 2A, the primary x-ray tube 108 may be positioned out of the way of the secondary x-ray tube 109, which may be in a desired operating position. In the stowed position, the focal point 262 of the primary x-ray tube 108 may be in a higher position than the focal point 264 of the secondary x-ray tube, as can be seen in FIG. 2A. The primary x-ray tube 108 may then be moved from the stowed position into a desired operating position for the primary x-ray tube 108 via the control assembly 144. Specifically, for example, rotation of the hand crank 150 in a first direction correspondingly rotates the ball screw 152 connected to linking member 158 and moves the first x-ray tube support 134 and the second x-ray tube support 142 in a first direction along the first track assembly 132. Movement of the first x-ray tube support 134 in the first direction along the first track assembly 132 also engages the first x-ray tube support 134 with the ramp assembly 138. Moving the first x-ray tube support 134 along the ramp assembly in the first direction moves the first x-ray tube support 134 as shown in a generally vertically downward direction as the first-x-ray tube support moves horizontally along the first track assembly 132. The hand crank may continue to be rotated until the primary x-ray tube 108 is in a desired operating position. In some embodiments, like the embodiment shown in FIG. 2B, the mounting assembly can be configured such that when the primary x-ray tube 108 is in the desired operating position, the focal point 262 of the primary x-ray tube is in the same position that the focal point 264 of the secondary x-ray tube 109 was when the secondary x-ray tube was in the desired operating position, as shown in FIG. 2A. In this way, because the focal points 262, 264 are in the same position, the position of a component to be imaged on the foundation platform does not have to be adjusted when switching between the primary x-ray tube 108 to the secondary x-ray tube 109. Rotation of the hand crank 150 in a reverse may similarly correspondingly rotate the ball screw 152 connected to linking member 158, moving the first x-ray tube support 134 and the second x-ray tube support 142 in a reverse or second direction along the first track assembly 132. Movement of the first x-ray tube support 134 in the reverse direction along the first track assembly 132 again engages the first x-ray tube support 134 with the ramp assembly 138. This time, moving the first x-ray tube support 134 along the ramp assembly in the reverse direction moves the first x-ray tube support 134 in a generally vertically upward direction as the first-x-ray tube support moves horizontally along the first track assembly 132. The hand crank may continue to be rotated until the primary x-ray tube 108 is in a stowed position. The secondary x-ray tube 109 may substantially simultaneously be caused to move horizontally along with the primary x-ray into the desired operating position. Again, in some embodiments, the mounting assembly can be configured such that when the secondary x-ray tube 109 is in the desired operating position, the focal point 264 of the secondary x-ray tube is in the same position that the focal point 262 of the primary x-ray tube 108 was when the primary x-ray tube was in the desired operating position. Additionally, when switching between x-ray tubes 108, 109 in this manner, undesirable or unintended contact between the x-ray tubes and the component to be imaged can be avoided. Moreover, when the primary 108 x-ray tube is in a stowed position, it may be stowed generally up and away from the component to be imaged, leaving more room for the component to be moved, tilted, or rotated with respect to the focal point 264 of the secondary x-ray tube 109 without interfering. In some embodiments, the primary x-ray tube 108 may be operated only when the primary x-ray tube is in the operating position and the secondary x-ray tube 109 is in the stowed position, and the secondary x-ray tube may be operated only when the secondary x-ray tube is in the operating position and the primary x-ray tube is in the stowed position.

Figure 3A:
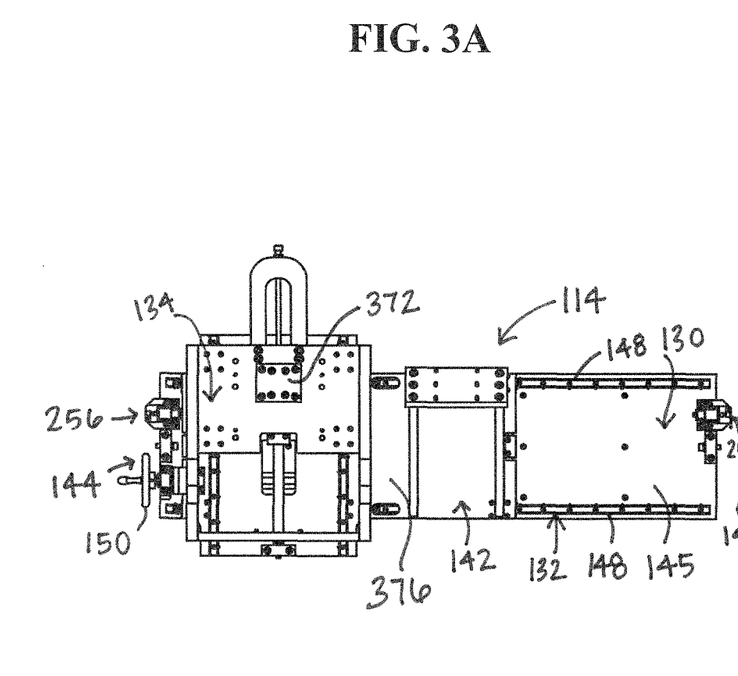
FIG. 3A shows a front view of one embodiment of the mounting assembly shown in FIG. 2A without the x-ray tubes.
Figure 3B:
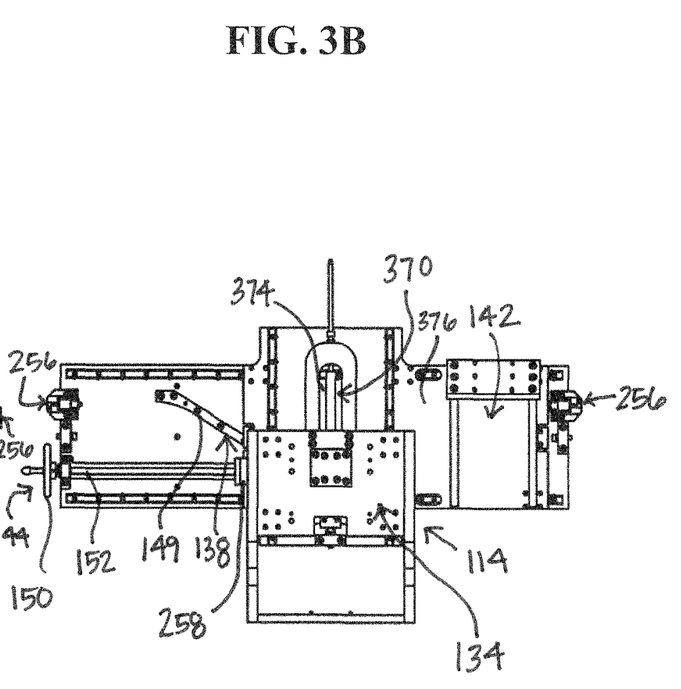
FIG. 3B shows a front view of the mounting assembly shown in FIG. 2B in without the x-ray tubes.

FIGS. 3A and 3B show a x-ray tube mounting assembly 114 in the positions shown in FIGS. 2A and 2B respectively but with the x-ray tubes not attached or illustrated. As shown in FIGS. 3A and 3B, the first x-ray tube support 134 may comprise a cam follower assembly 370. In at least the embodiment shown, the first x-ray tube support 134 may be engaged with the ramp assembly 138 via the cam follower assembly 370 to assist vertical movement of the first x-ray tube support 134. In some embodiments, the second x-ray tube support 142 may also be engaged with a ramp assembly and/or a cam follower assembly, if suitable, for positioning the x-ray tube mounted to the second x-ray tube support. The cam follower assembly 370 may comprise a cam follower 372 (also illustrated from a reverse side in FIG. 4B, discussed below) for engagement with the ramp 149 of the ramp assembly 138 and a vertical channel 374 for slidable vertical movement of the cam within the vertical channel 374 as the cam follower 372 moves along the ramp 149 of the ramp assembly 138. In at least one embodiment, the vertical channel 174 is disposed within a back plate 376 (described in further detail below) of the x-ray tube mounting assembly 114. As the control assembly 144 is actuated to move the first x-ray tube support 134 and second x-ray tube support 142 in a horizontal direction, the cam follower 372 slides along ramp 149 and moves within the vertical channel 374 in a vertical direction to move the first x-ray tube support 134 up or down depending on the direction of horizontal movement along the ramp 149. In at least one embodiment, when the first x-ray tube mounted to the first x-ray tube support 134 is in the stowed position, the cam follower 372 is positioned in a top or upper position within the vertical channel 374. In at least one embodiment, when the first x-ray tube mounted to the first x-ray tube support 134 is in the desired operating position, the cam follower 372 is positioned in a bottom or lower position within the vertical channel 374. In some embodiments, moving from the stowed position to the desired operating position for the primary x-ray tube 108 may move the cam follower 372 along the ramp 149 in a generally downward motion, and moving from the desired operating position to the stowed position for the primary x-ray tube may move the cam follower 372 along the ramp in a generally upward motion. In other embodiments, however, moving from the stowed position to the desired operating position for the primary x-ray tube 108 may move the cam follower 372 along the ramp 149 in a generally upward motion, while moving from the desired operating position to the stowed position for the primary x-ray tube may move the cam follower 372 along the ramp in a generally downward motion. The direction of the movement may depend on the positioning and configuration of the ramp 149 of the ramp assembly 138.

Figure 4A:
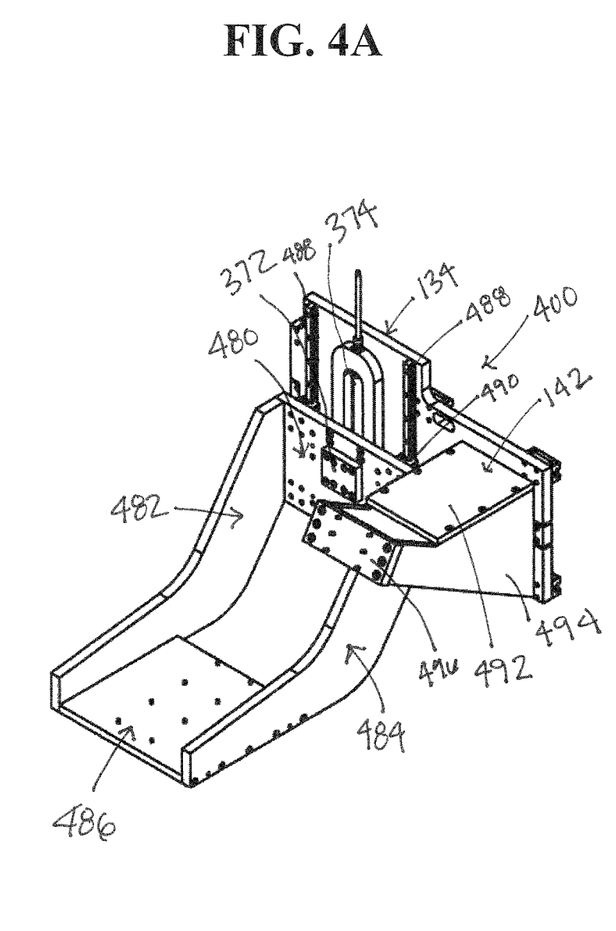
FIG. 4A shows an isometric view of one embodiment of an x-ray tube holder bracket.
Figure 4B:
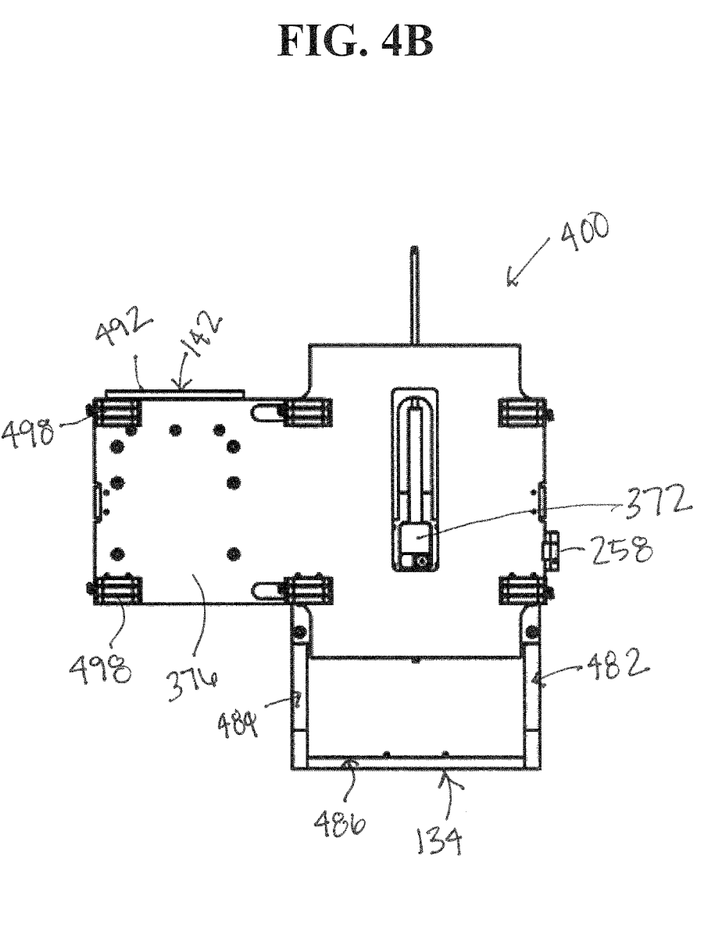
FIG. 4B shows a back view of the x-ray tube holder bracket shown in FIG. 4A.

FIGS. 4A and 4B show a perspective view and a back view, respectively, of an x-ray tube support bracket 400, according to one embodiment of the present disclosure, that comprises both the first x-ray tube support 134 and the second x-ray tube support 142 mounted to the back plate 376, such that the first x-ray tube support and the second x-ray tube support move horizontally as a unit. In one embodiment, The first x-ray tube support 134 may comprise a cam plate 480, a first side plate 482 connected to the cam plate 480, a second side plate 484 connected to the cam plate 480, and a bottom plate 486 connected to the first side plate 482 and the second side plate 484. In at least one embodiment, the first x-ray tube support 134 has a generally scooped configuration as shown in FIG. 4A. In one embodiment, when a primary x-ray tube 108 is mounted to the first x-ray tube support 134, the primary x-ray tube may at least partially rest on the bottom plate 486. However, other configurations of connection or attachment between the first x-ray tube support 134 and a primary x-ray tube 108 may be utilized, and the first x-ray tube support need not have a bottom plate 486 upon which a primary x-ray is required to rest. In some embodiments, the cam plate 480 may include the cam follower 372 mounted to or integrally formed with the cam plate, wherein the cam follower 372 extends outwardly from the back of the cam plate 480 through the vertical channel 374 to slidably engage with the ramp 149 of the ramp assembly 138 when mounted to the mounting bracket 130. In at least one embodiment, the back plate 376 may comprise one or more rails, tracks, or the like 488 that engage with one or more corresponding guides 490 on the back of the cam plate 480 to guide or assist with the vertical movement of the first x-ray tube support 134 via the cam assembly 370. The second x-ray tube support 142 may be mounted to the same side of the back plate 376 as the first x-ray tube support 134. The second x-ray tube support 142 may comprise a top plate 492, a first side plate 494 connected to the top plate 492, a second side plate connected to the top plate 492, and a mounting plate 496 connected to the first side plate 494 and the second side plate for mounting the secondary x-ray tube in at least one configuration. However, other configurations of connection or attachment between the second x-ray tube support 142 and a secondary x-ray tube 109 may be utilized. As shown in FIG. 4B, the back plate 376 may comprise one or more guides 498 that each engage with the first track assembly 132 on the mounting bracket 130. The one or more guides 498 may each be configured for sliding engagement of the x-ray tube support bracket 400 relative to the mounting bracket 130 along the first track assembly 132. The guides 498 may also be configured to hold or support the x-ray tube support bracket 400 on the mounting bracket 130 by, in one embodiment, gripping the rails of the first track assembly 132. For example, in at least one embodiment, each guide 498 may have a channel that grippingly receives at least one rail of the first track assembly 132. Of course, in other embodiments, the rail and gripping roles of the guides 498 and the first track assembly 132 may be reversed. For example, each guide 498 may alternatively have one or more ribs or other protrusions grippingly received by a channel of at least one rail of the first track assembly 132. Other mechanisms for providing both a mounting or gripping force between the guides 498 and track assembly 132, as well as permitting sliding or other similar traveling motion of the guides along the track assembly are also contemplated as part of the present disclosure.

Figure 5:
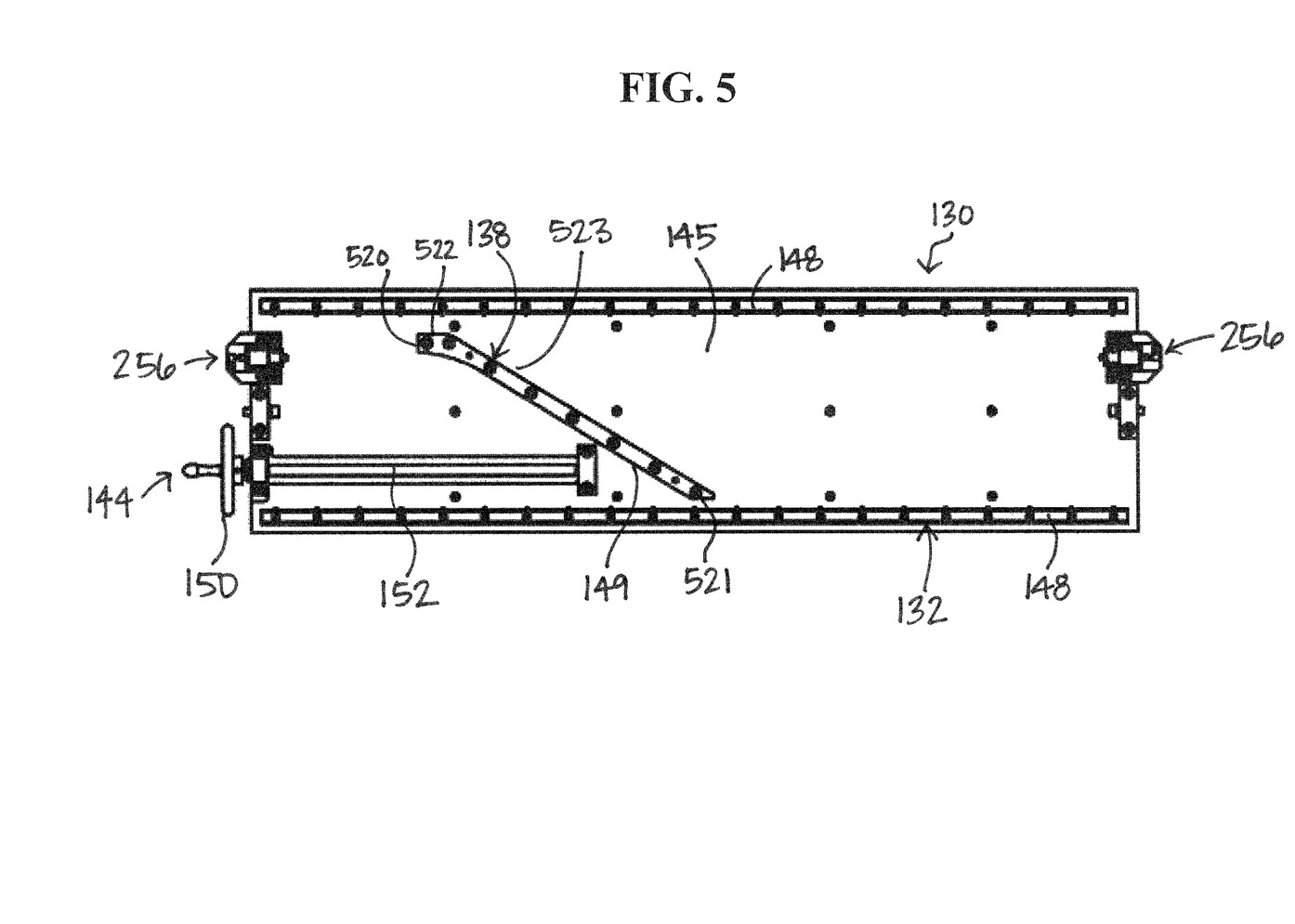
FIG. 5 shows a front view of one embodiment of a mounting bracket.

FIG. 5 shows a front view of one embodiment of the mounting bracket 130, which comprises first track assembly 132 having one or more rails 148, a ramp assembly 138 with at least one ramp 149, the control assembly 144 for engagement with the first x-ray tube support 134 or the back plate 376, and one or more stops 256. In at least one embodiment, the rails 148 extend substantially along the length of the mounting bracket 130 in a horizontal or longitudinal direction. In at least one embodiment, the stops 256 may positioned at each end of the mounting bracket 130. In at least one embodiment, the ramp assembly 138 may be positioned within a first half of the length of the mounting bracket corresponding to a horizontal travel path of the first x-ray tube support 134. The ramp 149 of the ramp assembly 138 may be positioned at a nonparallel angle between, and with respect to, the rails 148 of the track assembly 132. In at least one embodiment, the ramp 149 of the ramp assembly 138 may comprise two ends 520, 521. In some embodiments the ramp 149 may start at one end 520 and proceed through a generally horizontal portion 522, generally parallel with the rails 148 of the track assembly 132. An angled portion 523 may extend from the end of the horizontal portion 522, and may extend at a nonparallel angle with respect the rails 148 of the track assembly 132. In one embodiment, the straight portion 522 may be positioned on the mounting bracket 130 toward or nearer the top of the mounting bracket 130, between the rails 148. In one embodiment, the angled portion 523 may end at second end 521 toward or nearer the bottom of the mounting bracket 130, between the rails 148. In at least one embodiment, the control assembly 144 may comprise a hand crank 150, which rotates a ball screw 152 operably engaged with the linking member 258, shown for example in FIG. 4B. In at least one embodiment, the ball screw 152 has a length that extends between one end of the mounting bracket 130 and the ramp 149 of the ramp assembly 138. However, the ball screw 152 may extend further along the mounting bracket 130, if desired. The first x-ray tube support 134 and the second x-ray tube support 142 may be mounted to the rails 148 of the first track assembly 132, with the first x-ray tube support or the back plate 376, whichever embodiment may be the case, engaged with the control assembly 144 and the first x-ray tube support engaged with the ramp assembly 138 for movement of the first x-ray tube support and the second x-ray tube support along the mounting bracket 130 between stowed and operating positions, as previously described.

In use, when a user wishes to switch the primary x-ray tube 108 into the operating position and move the secondary x-ray tube 109 out of the operating position, the user can simply rotate the hand crank (or other control assembly) in a first direction to move the primary x-ray tube 108 in first horizontal and vertical directions such that the primary x-ray tube is positioned down and into the desired operating position. The secondary x-ray tube 109 may substantially simultaneously move in the same first horizontal direction into a stowed position. A component to be imaged on the platform may be positioned relative to the primary x-ray tube 108 while it is in the desired operating position, and the user may obtain one or more desired images of the component using the primary x-ray tube. When a user decides to switch from using the primary x-ray tube 108 to using the secondary x-ray tube 109, the user can simply rotate the hand crank (or other control assembly) in a second direction, opposite the first direction, to move the primary x-ray tube in second horizontal and vertical directions such that the primary x-ray tube is positioned up and away into its stowed position. The secondary x-ray tube 109 may substantially simultaneously move in the same second horizontal direction into the desired operating position. A component to be imaged on the platform may be positioned relative to the primary x-ray tube 108 while it is in the desired operating position, and the user may obtain one or more desired images of the component using the primary x-ray tube. As indicated above, in some embodiments, the imaging system or mounting assembly 114 thereof can be configured such that when the secondary x-ray tube 109 is moved into the desired operating position, the focal point of the second x-ray tube is automatically aligned to the same position that the focal point of the primary x-ray tube 108 was when it was in the desired operating position, and vice versa. In this way, the position of the component to be imaged on the platform need not be adjusted, in most cases, when switching between x-ray tubes.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

In the foregoing description, various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

We claim:

1. A component imaging system comprising:
    a frame comprising:
        a first upright;
        a second upright for mounting a x-ray detector; and
        a base operably connecting the first and second uprights; and
    a mounting assembly on the first upright, the mounting assembly comprising:
        a first x-ray tube support configured for supporting a first x-ray tube;
        a second x-ray tube support configured for supporting a second x-ray tube; and
        a control assembly for moving the first and second x-ray tube supports substantially simultaneously between a first position, wherein the first x-ray tube support is in an operating position and the second x-ray tube support is in a first stowed position not for operation of a second x-ray tube operably supported thereby, and a second position, wherein the second x-ray tube support is in the operating position and the first x-ray tube support is in a second stowed position not for operation of a first x-ray tube operably supported thereby.

2. The component imaging system of claim 1, wherein the first x-ray tube support is configured for supporting a x-ray tube of different focus source magnitude than the second x-ray tube support is configured to support.

3. The component imaging system of claim 2, wherein the mounting assembly further comprises a mounting bracket and means for slidable engagement between the mounting bracket and the first and second x-ray tube supports.

4. The component imaging system of claim 3, wherein the means for slidable engagement comprise a track operably connected with the mounting bracket and one or more guides operably connected with the first and second x-ray tubes, the one or more guides slidably engaging the track.

5. The component imaging system of claim 4, wherein the mounting bracket comprises a ramp positioned at a nonparallel angle to the track.

6. The component imaging system of claim 5, wherein the first x-ray tube support comprises a cam follower for engaging with the ramp as the first x-ray tube support is slidingly repositioned in a first direction along the track.

7. The component imaging system of claim 6, wherein engagement of the cam follower with the ramp as the first x-ray tube support is slidingly repositioned in the first direction along the track causes the first x-ray tube support to additionally move in a direction nonparallel to the first direction.

8. The component imaging system of claim 7, wherein the direction nonparallel to the first direction is perpendicular to the first direction.

9. The component imaging system of claim 1, configured such that in the first position, a focal point of a first x-ray tube supported by the first x-ray tube support is in substantially the same position as is a focal point of a second x-ray tube supported by the second x-ray tube support in the second position.

10. The component imaging system of claim 1, wherein the control assembly comprises a hand crank and a ball screw.

11. A x-ray tube mounting assembly comprising:
a mounting bracket;
a first x-ray tube support configured for supporting a first x-ray tube;
a second x-ray tube support configured for supporting a second x-ray tube; and
a control assembly for moving the first and second x-ray tube supports substantially simultaneously between a first position along the mounting bracket,
wherein the first x-ray tube support is in an operating position and the second x-ray tube support is in a first stowed position not for operation of a second x-ray tube operably supported thereby, and a second position, wherein the second x-ray tube support is in the operating position and the first x-ray tube support is in a second stowed position not for operation of a first x-ray tube operably supported thereby.

12. The mounting assembly of claim 11, wherein the first x-ray tube support is configured for supporting a x-ray tube of different focus source magnitude than the second x-ray tube support is configured to support.

13. The mounting assembly of claim 12, further comprising means for repositioning the first and second x-ray tube supports in a first direction along the mounting bracket.

14. The mounting assembly of claim 13, wherein the mounting bracket comprises a ramp positioned at a nonparallel angle to the first direction.

15. The mounting assembly of claim 14, wherein the first x-ray tube support comprises a cam follower for engaging with the ramp as the first x-ray tube support is repositioned in the first direction along the mounting bracket.

16. The mounting assembly of claim 15, wherein engagement of the cam follower with the ramp as the first x-ray tube support is repositioned in the first direction along the track causes the first x-ray tube support to be additionally repositioned in a direction nonparallel to the first direction.

17. The mounting assembly of claim 16, wherein the direction nonparallel to the first direction is perpendicular to the first direction.

18. The mounting assembly of claim 11, configured such that in the first position, a focal point of a first x-ray tube supported by the first x-ray tube support is in substantially the same position as is a focal point of a second x-ray tube supported by the second x-ray tube support in the second position.

19. A method for positioning a first x-ray tube and a second x-ray tube relative to a component to be imaged in a digital radiography or computed tomography imaging system, the method comprising adjusting the position of a first x-ray tube support, supporting the first x-ray tube, from a stowed position to an operating position by moving the first x-ray tube support along an angled ramp assembly, wherein a focal point of the first x-ray tube moves from a first position in the stowed position to a second position in the operating position, wherein the second position of the focal point of the first x-ray tube is substantially the same as a position of the focal point of the second x-ray tube when the first x-ray tube is in the stowed position.

20. The method of claim 19, wherein adjusting the position of the first x-ray tube support comprises moving the first x-ray tube support generally simultaneously in at least two non-parallel directions, and the method further comprises generally simultaneously moving the second x-ray tube support in at least one of the non-parallel directions.

* * * * *